United States Patent [19]

Saito et al.

[11] 4,371,711

[45] Feb. 1, 1983

[54] PROCESS FOR PRODUCING 4-HYDROXYCYCLOPENTENONES

[75] Inventors: Kenji Saito, Toyonaka; Hiroshi Yamachika, Ibaraki, both of Japan

[73] Assignee: Sumitomo Chemical Company, Limited, Osaka, Japan

[21] Appl. No.: 151,603

[22] Filed: May 20, 1980

[30] Foreign Application Priority Data

May 30, 1979 [JP] Japan ................... 54-67689
May 30, 1979 [JP] Japan ................... 54-67690
May 30, 1979 [JP] Japan ................... 54-67691
May 31, 1979 [JP] Japan ................... 54-68495

[51] Int. Cl.³ .............. C07C 45/29; C07C 45/45; C07C 45/59; C07C 45/67
[52] U.S. Cl. .................. 568/310; 568/341; 568/347; 568/315; 568/316; 568/348
[58] Field of Search ............... 568/347, 338, 357, 379, 568/341, 344, 393, 878, 361, 322, 348, 310, 315, 316

[56] References Cited

U.S. PATENT DOCUMENTS

| | | | |
|---|---|---|---|
| 3,775,492 | 11/1973 | Kierstead et al. ............. | 568/348 |
| 3,931,327 | 1/1976 | Stricker et al. ............... | 568/344 |
| 3,932,510 | 1/1976 | Muller et al. ................. | 568/341 |
| 3,981,920 | 9/1976 | Buchi ........................... | 568/379 |

OTHER PUBLICATIONS

Peancatelli et al, Tetrahedron, vol. 35, pp. 135-138 (1979).

Kharasch et al., "Grignard Reactions of Nonmetallic Substances," pp. 138-144 (1954); Prentice-Hall, Inc.

*Primary Examiner*—James H. Reamer
*Attorney, Agent, or Firm*—Stevens, Davis, Miller & Mosher

[57] ABSTRACT

A method of producing a 4-hydroxycyclopentenone represented by the formula,

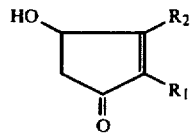

wherein $R_1$ is an alkyl, alkenyl, alkynyl, cycloalkyl, thienyl, phenyl, p-methylbenzyl or benzyl group and $R_2$ is an alkyl, alkenyl or alkynyl group having 6 or less carbon atoms, which comprises reacting a furylcarbinol compound of the formula,

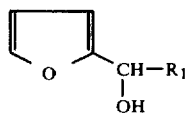

wherein $R_1$ is as defined above, in the presence of an acid in a mixed solvent of water and an organic solvent, to obtain a cyclopentenone compound of the formula,

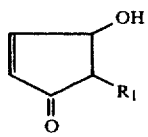

wherein $R_1$ is as defined above; reacting the cyclopentenone compound in the presence of an oxidizing agent to obtain a cyclopentendione compound of the formula,

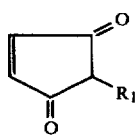

wherein $R_1$ is a defined above; reacting the cyclopentendione compound with a Grignard reagent of the formula,

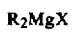

$R_2MgX$ wherein $R_2$ is as defined above and X is chlorine, bromine or iodine atom, to obtain an oxocyclopentene compound of the formula,

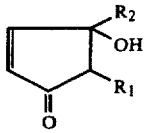

wherein $R_1$ and $R_2$ are as defined above; and reacting the cyclopentenone compound in the presence of a base.

The 4-hydroxycyclopentenones are useful intermediates of agricultural chemicals.

3 Claims, No Drawings

PROCESS FOR PRODUCING 4-HYDROXYCYCLOPENTENONES

This invention relates to a method of producing 4-hydroxycyclopentenones (hereinafter referred to as cyclopentenolons for brevity). More particularly, it relates to a method of producing cyclopentenolons which are useful intermediates for pesticides and are represented by the formula (I),

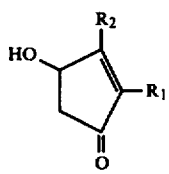
(I)

wherein $R_1$ is an alkyl, alkenyl, alkynyl, cycloalkyl, thienyl, phenyl, p-methylbenzyl or benzyl group and $R_2$ is an alkyl, alkenyl or alkynyl group having 6 or less carbon atom.

Allethrin, known as a useful pesticide, was invented by M. S. Schechter and has been widely used all over the world because of its excellent insecticidal activity and low toxicity. Synthesis of the compounds has been the target of various reseaches. The synthetic studies include also various proposals as to the method of synthesis for the alcohol components and some of which are now employed in actual production.

The proposed methods, however, have disadvantages of insufficient yield, complicated procedure and, in addition, accompanying environmental pollution problems. For these reasons, they are not entirely satisfactory from the standpoint of commercial production. Of the proposed methods, those for the synthesis of allethrolons through furan compounds, have been described, for example, by G. Piancatelli et al. [Tetrahedron, 34, 2775 (1978)] and T. Shono et al. [Chemistry Letters, 1249 (1976)]. Reaction scheme of G. Piancatelli et al.:

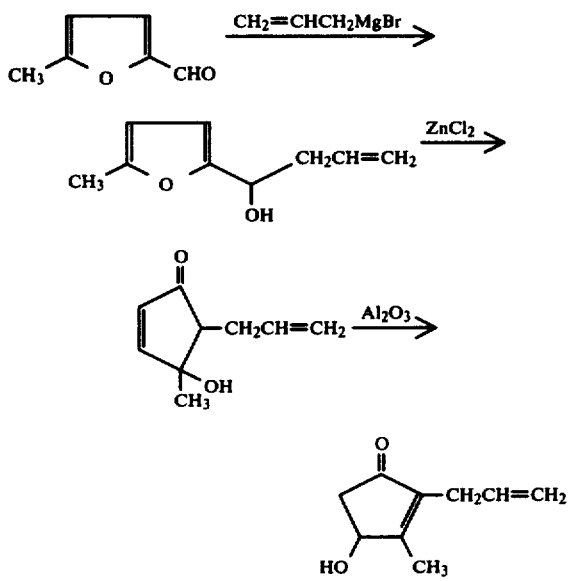

Reaction scheme of T. Shono et al.:

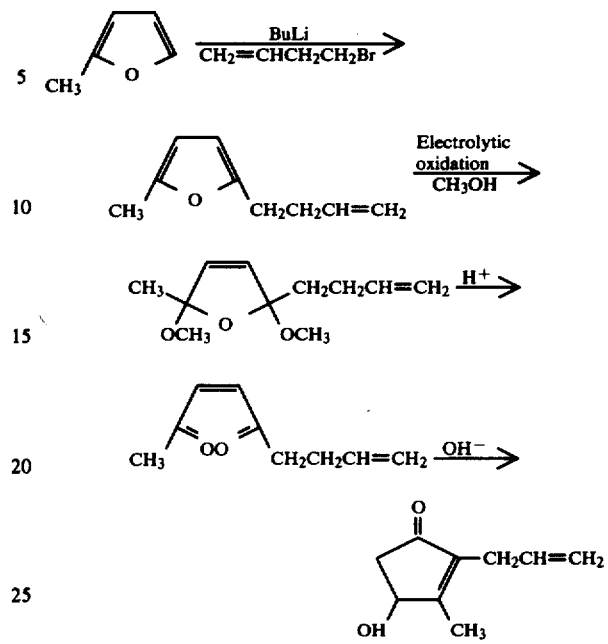

Both methods, however, are not satisfactory from the standpoint of large scale production, because of difficult availability and expensiveness of materials to be used, complicated procedures and unsatisfactory yields.

Under the circumstances, the present inventors conducted extensive studies on the method of producing the cyclopentenolons and, as a result, found a novel method for advantageously producing the cyclopentenolons.

The present invention provides a method for producing cyclopentenolons represented by the aforementioned formula (I), which comprises, (1) a first step (hereinafter referred to as step A) of preparing a cyclopentenone compound of the formula (III),

(III)

wherein $R_1$ is as defined above, by reacting a furylcarbinol compound of the formula (II),

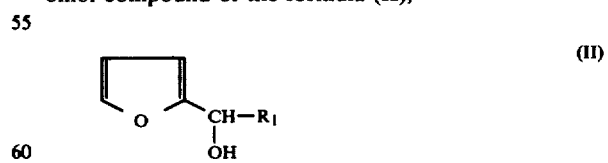
(II)

wherein $R_1$ is as defined above, in the presence of an acid in a mixed solvent of water and an organic solvent, said furylcarbinol compound being obtained by reacting furfural with a Grignard reagent of the formula (VI),

$R_1MgX$ (VI)

wherein $R_1$ is as defined above and X is chlorine, bromine or iodine atom;

(2) a second step (hereinafter referred to as step B) of preparing a cyclopentenedione compound of the formula (IV),

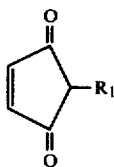
(IV)

wherein $R_1$ is as defined above, by oxidizing said cyclopentenone compound (III);

(3) a third step (hereinafter referred to as step C) of preparing an oxocyclopentene compound of the formula (V),

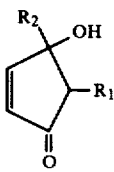
(V)

wherein $R_1$ and $R_2$ are as defined above, by reacting a Grignard reagent of the formula (VII), $R_2MgX$ (VII)

wherein $R_2$ and X are as defined above, with said cyclopentenedione compound (IV); and (4) a fourth step (hereinafter referred to as step D) of preparing cyclopentenolons of the formula (I) by reacting said oxocyclopentene compound (V) in the presence of a base.

In the cyclopentenolon compounds of the formula (I), examples of $R_1$ include alkyl groups such as methyl, ethyl, propyl and hexyl; alkenyl groups such as allyl and 2-butenyl; alkynyl groups such as propargyl and ethynyl; cycloalkyl groups such as cyclopentyl and cyclohexyl; thienyl groups, phenyl groups, p-methylbenzyl group and benzyl group. Examples of $R_2$ include alkyl groups such as methyl, ethyl and n-hexyl; alkenyl groups such as allyl, 3-butenyl and 5-hexenyl; and alkynyl groups such as propargyl, 3-butynyl and 3-hexynyl.

The process of the present invention is illustrated in detail as follows;

STEP A:

Typical acids employed in step A are formic acid, trichloroacetic acid, dichloroacetic acid, phosphoric acid, polyphosphoric acid and pyrophosphoric acid. These acids are used in an amount in the range of 0.3 to 4.0, preferably 0.3 to 1.5 times the weight of a furylcarbinol of the formula (II).

Suitable organic solvents are acetone, dioxane, methyl ethyl ketone, tetrahydrofuran and dimethyl sulfoxide. In order to minimize formation of by-products, these organic solvents are used in an amount of preferably 30 times or more the weight of furylcarbinol compounds used as starting materials. In this reaction, water is used preferably in an amount of 10% or more of the total weight of water and organic solvents.

The reaction temperature is generally in the range of 40° to 110° C. It is also possible, if necessary, to terminate the reaction at a conversion of the starting furylcarbinol compound in the range of 40 to 80%, preferably 50 to 60% and recover the unreacted starting material by a separation and purification means such as distillation to be used again. Such a mode of reaction results in an improvement in the yield and purity of the product.

STEP B

The oxidizing agents employed in step B include chromic anhydride, chromates, dichromic acid, dichromates, chromyl chloride, chromate esters, manganese dioxide, activated manganese dioxide, potassium permanganate, aluminum isopropoxide, aluminum tert-butoxide, lead tetraacetate, ruthenium tetraoxide, N-halocarboxylic acid amide, oxygen, hydrogen peroxide, organic peroxides, halogen, nitric acid, nitrous acid, dimethyl sulfoxide, quinones, silver (I) carbonate, silver (II) carbonate, copper (II) oxide, copper (II) hydroxide, cerium (IV) salts, vanadates, coblat (II) salts and ozone. Of these, preferred are chromates, dichromic acid, dichromates, chromyl chloride, chromate esters, chromic oxide-pyridine complex, N-halocarboxylic acid amides, oxygen, aluminum tertbutoxide, and aluminum isopropoxide.

The kind of the reaction solvent to be used depends on the type of oxidizing agent. For example, suitable solvents are petroleum ether, ether, acetone, methylene chloride, pentane, benzene, chloroform and 5% methanol-chloroform solution for manganese dioxide and activated manganese dioxide; ether-water mixture, benzene, acetone, pyridine, water, dilute sulfuric acid, acetic acid, tetrahydrofuran, dioxane, ether, chlorobenzene and carbon tetrachloride for chromic acids; tert-butyl alcohol-pyridine solution, aqueous acetone and aqueous dioxane for N-halocarboxylic acid amides; n-heptane, petroleum benzine, ethyl acetate, dioxane, acetone and water for oxygen; benzene, toluene, benzene-acetone solution and toluene-acetone solution for aluminum tert-butoxide and aluminum isopropoxide; dioxane, carbon tetrachloride, tetrahydrofuran and ether for 2,3-dichloro-5,6-dicyano-1,4-benzoquinone; and water, acetone, ethanol, tert-butylcarbinol, pyridine, chloroform, isooctane, benzene, petroleum ether and methylcyclohexane for potassium permanganate.

Although not subject to any special limitation, the reaction temperature is generally in the range of −20° to 180° C., preferably 0° to 120° C.

When the oxidation is carried out with oxygen, the reaction can be caused to proceed efficiently by use of platinum-activated carbon or platinum black as the catalyst.

STEP C

The Grignard reagent of the formula (VII) for use in step C can be prepared in a customary manner from metallic magnesium and a halide of the general formula (VIII), $R_2X$ (VIII)

wherein $R_2$ and X are as defined above. The Grignard reaction also proceeds easily in a customary manner.

STEP D

The bases employed in step D include hydroxides, carbonates, hydrogencarbonates and acetates of alkali metals such as sodium and potassium; basic salts such as hydroxides, carbonates, hydrogencarbonates and acetates of alkaline earth metals such as calcium and barium; amines such as triethylamine and pyridine; basic ion exchange resins and alumina.

The amounts used of the bases are generally 0.5 to 30, preferably 2 to 20 times the weight of the oxocyclopentene compound (V) in the case of alumina and generally 0.01 to 10, preferably 0.05 to 1 mole per mole of the oxocyclopentene compound (V) in the cases of other bases.

The suitable solvent systems are water and mixtures of water and organic solvents. The organic solvents include alcohols such as methanol and ethanol; ethers such as diethyl ether, tetrahydrofuran and dimethoxyethane; halogenated hydrocarbons such as chloroform and trichloroethylene; non-protonic polar solvents such as dimethylformamide and dimethyl sulfoxide; aromatic hydrocarbons such as benzene and toluene; ketones such as acetone and methyl ethyl ketone; and mixtures of these compounds. The reaction temperature in the case of alumina is 0° to 150° C., usually 20° to 70° C. and that in the cases of other bases is 0° to 200° C., usually 10° to 150° C. The reaction time is generally 10 to 48 hours for alumina and 1 to 4 hours for other bases.

The invention is illustrated below in further detail with reference to Examples, but the invention is, of course, not limited to the Examples.

EXAMPLE 1

Into 350 ml of a water-acetone (1:6 by volume) mixture, was dissolved 10 g of 2-(1-hydroxy-3-butenyl)furan. To the solution heated at 55° C. under reflux, was added dropwise 6.6 g of polyphosphoric acid. After having been stirred at 55° C. for 96 hours, the reaction mixture was freed from the acetone by distillation and the residue was extracted twice with 300 ml of ether. The extract solution was washed with an aqueous sodium hydrogencarbonate solution, then with saturated aqueous sodium chloride solution, dried over anhydrous sodium sulfate, and freed from the solvent by distillation to obtain 8.5 g of a concentrate. The concentrate was purified by a column chromatography using 100 g of a silica gel (Wako Gel C-200) and a toluene-ether (2:1 by volume) mixture as eluent, to obtain 4.3 g (43% yield) of 4-hydroxy-5-allyl-2-cyclopentenone.

NMR spectral data (CCl$_4$; internal standard, TMS, $\delta$ ppm, 60 MHz):

7.48 (d of d, 1H, 3-H)
6.08 (d, 1H, 2-H)
5.70 (complex m, 1H, —CH$_2$—C$\underline{H}$=CH$_a$H$_b$)
5.13 (m, 1H, —CH$_2$—CH=C$\underline{H}_a$H$_b$)
4.90 (m, 1H, —CH$_2$—CH=CH$_a\underline{H}_b$)
4.59 (broad s, 1H, 4-H)
4.42 (broad s, 1H, 4-O$\underline{H}$)
2.32 (m, 3H, 5-H & —C$\underline{H}_2$—CH=CH$_a$H$_b$)

EXAMPLE 2

Into 350 ml of a water-acetone (1:6 by volume) mixture, was dissolved 10 g of 2-(1-hydroxy-3-butenyl)furan. To the solution heated at b 55° C. under reflux, was added dropwise 6.6 g of polyphosphoric acid. After having been stirred at 55° C. for 48 hours, the reaction mixture was stripped of the acetone by distillation and the residue was extracted twice with 300 ml of ether. The extract solution was washed with an aqueous sodium hydrogencarbonate solution, then with saturated sodium chloride solution, dried over anhydrous sodium sulfate, and freed from the solvent by distillation to obtain 9.5 g of a concentrate. On distillation of the concentrate, there were obtained 4.2 g of 2-(1-hydroxy-3-butenyl)furan (b.p. 78° C./10 mmHg) and 3.8 g (65.5% yield based on consumed starting material) of the intended 4-hydroxy-5-allyl-2-cyclopentenone (b.p. 97° C./0.7 mmHg).

EXAMPLE 3

A concentrate (8.8 g) was obtained in the same manner as in Example 1, except that 2-(1-hydroxy-3-butenyl)furan was used in place of the 2-(1-hydroxy-3-butenyl)furan. The concentrate was purified by column chromatography in the same manner as in Example 1 to obtain 4.6 g (46% yield) of 4-hydroxy-5-propargyl-2-cyclopentenone.

Elementary analysis: C, 70.6%; H, 5.9%

EXAMPLE 4

To a solution of 1.9 g of chromic anhydride in 5.4 g of water, was added 1.6 ml of concentrated sulfuric acid, while cooling in ice. The mixture was stirred to form a solution. The solution was added dropwise to a solution of 3.7 g of 4-hydroxy-5-allyl-2-cyclopentenone in 8 ml of acetone over a period of 2 hours while cooling in ice. After completion of the dropwise addition, stirring was continued for another hour. The reaction mixture was extracted with ether and the ether layer was washed successively with an aqueous sodium hydrogencarbonate solution and a saturated aqueous sodium chloride solution, dried over anhydrous sodium sulfate, and the solvent was removed by distillation to obtain 3.2 g of a concentration residue. The residue was purified by column chromatography using 40 g of a silica gel (Wako Gel C-200) and an ethyl acetate-n-hexane (2:3 by volume) mixture as eluent to obtain 2.91 g (80.0% yield) of 4-keto-5-allyl-2cyclopentenone. n$_D^{20}$=1.5065

NMR spectral data (CDCl$_3$; internal standard, TMS; $\delta$, ppm; 90 MHz):

7.32 (s, 2H, 2-H & 3-H)
5.65 (complex m, 1H, —CH$_2$—C$\underline{H}$=CH$_a$H$_b$)
5.11 (m, 1H, —CH$_2$—CH=C$\underline{H}_a$H$_b$)
4.95 (m, 1H, —CH$_2$—CH=CH$_a\underline{H}_b$)
2.88 (m, 1H, 5-H)
2.52 (t, 2H, —C$\underline{H}_2$—CH=CH$_a$H$_b$)

EXAMPLE 5

Into 200 ml of chloroform, was dissolved 4.0 g of 4-hydroxy-5-propargyl-2-cyclopentenone. To the solution, was added 25 g of activated manganese dioxide and the mixture was stirred at room temperature for 4 hours. The reaction mixture was filtered and the residue on the filter was washed thoroughly with chloroform. The filtrate together with the washings was concentrated to obtain 3.6 g (91% yield) of 4-keto-5-propargyl-2-cyclopentenone, pale yellow in color.

Elementary analysis: C, 71.6%; H, 4.5%

EXAMPLE 6

Into a mixture of 150 ml of dried benzene and 100 ml of acetone, was dissolved 1.5 g of 4-hydroxy-5-allyl-2-cyclopentenone. After adding 3 g of freshly distilled aluminum isoproproxide, the mixture was heated under reflux for 12 hours. The reaction mixture was cooled to room temperature, washed twice with 30% sulfuric acid, then with water until the washings had become neutral. After drying over anhydrous sodium sulfate, the mixture was stripped of the solvent by distillation and the residue was distilled in vacuo to obtain 1.2 g (81% yield) of 4-keto-5-allyl-2-cyclopentenone boiling at 53° C./4 mmHg.

EXAMPLE 7

Into 6 ml of dioxane, were dissolved 500 mg of 4-hydroxy-5-allyl-2-cyclopentenone and 450 mg of 2,3-dichloro-5,6-dicyano-1,4-benzoquinone. The solution was left standing at room temperature for 16 hours and the precipitated 2,3-dichloro-5,6-dicyanohydroquinone was collected by filtration and washed with methylene chloride. The filtrate together with the washings was concentrated. The concentration residue was dissolved in 50 ml of methylene chloride, washed with a 10% aqueous sodium hydroxide solution, then with water until the washings had become neutral. The residue thus treated was dried over anhydrous sodium sulfate, stripped of the solvent by distillation, and purified by column chromatography using 20 g of a silica gel (Wako Gel C-200) and an ethyl acetate-n-hexane (2:3 by volume) mixture as eluent, to obtain 450 mg (91% yield) of 4-keto-5-allyl-2-cyclopentenone.

EXAMPLE 8

Into a flask, were placed 0.8 g of metallic magnesium and 20 ml of ether. To the flask, was added dropwise 1.9 g of methyl iodide over a period of 2 hours at room temperature while stirring. After the dropwise addition, the mixture was stirred for another hour. The resulting Grignard reagent was added dropwise with stirring to a solution of 2.0 g of 4-keto-5-allyl-2-cyclopentenone in 10 ml of ether over a period of 2 hours at room temperature. After the dropwise addition, the mixture was stirred for another hour. To the mixture while cooling in ice, was added 30 ml of a saturated aqueous ammonium chloride solution. After having been stirred for one hour, the reaction mixture was allowed to separate into an ether layer and an aqueous layer. The aqueous layer was extracted twice with 30 ml of ether. The washings were combined with the above ether layer and washed successively with an aqueous sodium hydrogencarbonate solution and saturated aqueous sodium chloride solution. The ether layer thus treated was dried over anhydrous sodium sulfate and stripped of the ether by distillation to obtain 2.2 g of a residue. The residue was purified by column chromatography using 20 g of a silica gel (Wako Gel C-200) and a toluene-ether (2:1 by volume) mixture as eluent, to obtain 1.5 g (67% yield) of 4-hydroxy-4-methyl-5-allyl-2-cyclopentenone.

NMR data (CCl$_4$; internal standard, TMS; δ ppm; 60 NMz):

7.32 (d, 1H, 3-H)

5.92 (d, 1H, 2-H)

5.31 (complex m, 1H, —CH$_2$—C$\underline{H}$=CH$_a$H$_b$)

5.12 (m, 1H, —CH$_2$—CH=CH$_a\underline{H_b}$)

4.93 (m, 1H, —CH$_2$—CH=C$\underline{H_a}$H$_b$)

4.12 (broad s, 1H, 4-O$\underline{H}$)

2.37 (m, 3H, 5-H & —C$\underline{H_2}$—CH=CH$_a$H$_b$)

1.28 (s, 3H, 4-C$\underline{H_3}$)

EXAMPLE 9

Twenty grams of a 300-mesh activated alumina (Wako Junyaku Co.) for use in column chromatography was suspended in 100 ml of a toluene-ether (1:1 by volume) mixture admixed with 2.4 g of water. To the suspension, was added 4.0 g of 4-hydroxy-4-methyl-5-allyl-2-cyclopentenone. The suspension was stirred at 30° C. for 24 hours and the alumina was separated by filtration. The separated alumina was extracted three times with 50 ml of a toluene-ether (1:1 by volume) mixture. The extract solutions were combined with the filtrate and concentrated. The concentrate was fractionally distilled in vacuo to obtain 2.5 g (62.5% yield) of 2-allyl-3-methyl-4-hydroxy-2-cyclopentenone boiling at 155° C./1 mmHg.

NMR data (CDCl$_3$; internal standard, TMS; δ ppm; 90 MHz):

5.71 (complex m, 1H, —CH$_2$—C$\underline{H}$=CH$_a$H$_b$)

5.06 (m, 1H, —CH$_2$—CH=CH$_a\underline{H_b}$)

4.93 (m, 1H, —CH$_2$—CH=C$\underline{H_a}$H$_b$)

4.74 (broad d, 1H, 4-H)

3.94 (broad s, 1H, 4-O$\underline{H}$)

2.96 (d, 2H, —C$\underline{H_2}$—CH=CH$_a$H$_b$)

2.85 (d of d, 1H, 5-H)

2.27 (d of d, 1H, 5-H)

2.11 (s, 3H, 3-C$\underline{H_3}$)

EXAMPLE 10

In 200 ml of a 5% aqueous sodium hydrogen-carbonate solution, was dissolved 29 g of 4-hydroxy-4-methyl-5-allyl-2-cylcopentenone. The solution was heated with stirring under reflux for one hour. After having been allowed to cool, the reaction mixture was extracted three times with chloroform. The extract solution was dried over anhydrous magnesium sulfate and freed from the chloroform by distillation. The residue was distilled in vacuo to obtain 21.7 g (75% yield) of 2-allyl-3-methyl-4-hydroxy-2-cyclopentenone boiling at 155° C./1 mmHg.

EXAMPLES 11 and 17

The procedures in Examples 11 to 13 were similar to those in Examples 2, 4, 8 and 9 and the procedures in Examples 14 to 17 were similar to those in Examples 2, 4, 8 and 10. The results obtained were as shown in the following table.

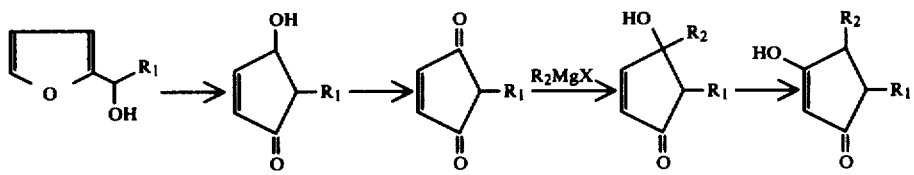

| Example No. | R₁ | yield*¹ (%) | yield (%) | Elementary analysis C% H% S% | R₂ | X | yield (%) | Elementary analysis C% H% S% | yield (%) | Elementary analysis C% H% S% |
|---|---|---|---|---|---|---|---|---|---|---|
| 11 | CH≡CCH₂— | 65 | 72 | 71.6 4.5 — | CH₃— | I | 50 | 72.0 6.7 — | 70 | 72.1 6.6 — |
| 12 | CH₃CH₂— | 75 | 85 | 67.7 6.5 — | CH₃— | I | 51 | 68.5 8.6 — | 62 | 68.5 8.7 — |
| 13 | 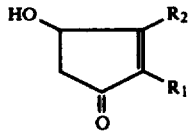 | 85 | 73 | 74.1 7.9 — | CH≡CCH₂— | Br | 60 | 77.0 8.3 — | 70 | 77.1 8.3 — |
| 14 | phenyl | 60 | 90 | 76.7 4.7 — | CH₂=CHCH₂— | Br | 55 | 78.5 6.6 — | 85 | 78.4 6.6 — |
| 15 | benzyl | 71 | 91 | 77.4 5.4 — | CH₂=CHCH₂— | Cl | 54 | 78.9 7.1 — | 82 | 78.8 7.0 — |
| 16 | CH₃—C₆H₄—CH₂— | 65 | 90 | 78.0 6.0 — | CH₃— | I | 53 | 77.7 7.5 — | 74 | 77.5 7.5 — |
| 17 | 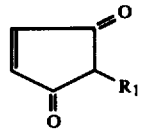 | 75 | 93 | 60.7 3.4 17.9 | CH₃— | I | 58 | 61.8 5.2 16.5 | 77 | 61.8 5.2 16.7 |

Note:
*yield (%) based on consumed starting material.

What is claimed is:

1. A method of producing a 4-hydroxycyclopentenone represented by the formula

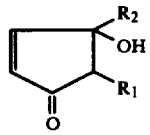

wherein R₁ is an alkyl, alkenyl, alkynyl, cycloalkyl, thienyl, phenyl, p-methylbenzyl or benzyl group and R₂ is an alkyl, alkenyl or alkynyl group having 6 or less carbon atoms, which comprises reacting a cyclopentendione compound of the formula,

wherein R₁ is as defined above, with a Grignard reagent of the formula,

R₂MgX wherein R₂ is as defined above and X is chlorine, bromine or iodine, to obtain an oxocyclopentene compound of the formula wherein R₁ and R₂ are as defined above; and reacting the oxocyclopentene compound in the presence of a base selected from the group consisting of hydroxides, carbonates, bicarbonates and acetates of sodium and potassium; basic salts of hydroxides, carbonates, bicarbonates and acetates of calcium and barium; triethylamine or pyridine; and basic ion exchange resins; in an amount of from 0.01 to 10 moles per mole of the oxocyclopentene compound at 0° to 200° C., or in the presence of alumina in an amount of from 0.5 to 30 times the weight of the oxocyclopentene compound at 0° to 150° C.

2. A method of producing a 4-hydroxycyclopentenone represented by the formula,

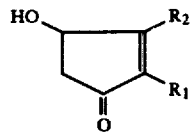

wherein R₁ is an alkyl, alkenyl, alkynyl, cycloalkyl, thienyl, phenyl, p-methylbenzyl or benzyl group and R₂ is an alkyl, alkenyl or alkynyl group having 6 or less carbon atoms, which comprises oxidizing a cyclopentenone compound of the formula,

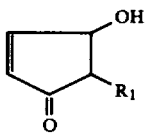

wherein $R_1$ is as defined above, in the presence of an oxidizing agent selected from the group consisting of chromic anhydride, chromates, dichromic acid, dichromates, chromyl chloride, chromate esters, chromic oxide-pyridine complex, manganese dioxide, activated manganese dioxide, potassium permanganate, aluminum isopropoxide, aluminum tert-butoxide, lead tetraacetate, ruthenium tetraoxide, N-halocarboxylic acid amide, oxygen, hydrogen peroxide, organic peroxides, halogen, nitric acid, nitrous acid, dimethyl sulfoxide, quinones, silver (I) carbonate, silver (II) carbonate, copper (II) oxide, copper (II) hydroxide, cerium (IV) salts, vanadates, cobalt (II) salts and ozone, at −20° to 180° C., to obtain a cyclopentendione compound of the formula,

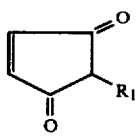

wherein $R_1$ is as defined above; reacting the cyclopentendione compound with a Grignard reagent of the formula,

wherein $R_2$ is as defined above and X is chlorine, bromine or iodine, to obtain an oxocyclopentene compound of the formula,

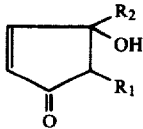

wherein $R_1$ and $R_2$ are as defined above; and reacting the oxocyclopentene compound in the presence of a base selected from the group consisting of hydroxides, carbonates, bicarbonates and acetates of sodium and potassium; basic salts of hydroxides, carbonates, bicarbonates and acetates of calcium and barium; triethylamine or pyridine; and basic ion exchange resins; in an amount of from 0.01 to 10 moles per mole of the oxocyclopentene compound at 0° to 200° C., or in the presence of alumina in an amount of from 0.5 to 30 times the weight of the oxocyclopentene compound at 0° to 150° C.

3. A method of producing a 4-hydroxycyclopentenone represented by the formula,

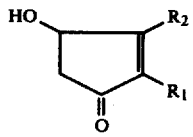

wherein $R_1$ is an alkyl, alkenyl, alkynyl, cycloalkyl, thienyl, phenyl, p-methylbenzyl or benzyl group and $R_2$ is an alkyl, alkenyl or alkynyl group having 6 or less carbon atoms, which comprises reacting a furylcarbinol compound of the formula,

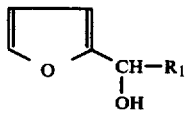

wherein $R_1$ is as defined above, in the presence of an acid selected from the group consisting of formic acid, trichloroacetic acid, dichloroacetic acid, phosphoric acid, polyphosphoric acid and pyrophosphoric acid, in a mixed solvent of water and an organic solvent selected from the group consisting of acetone, dioxane, methyl ethyl ketone, tetradyrofuran and dimethyl sulfoxide, to obtain a cyclopentenone compound of the formula,

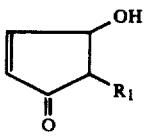

wherein $R_1$ is as defined above; oxidizing the cyclopentenone compound in the presence of an oxidizing agent selected from the group consisting of chromic anhydride, chromates, dichromic acid, dichromates, chromyl chloride, chromate esters, chromic oxide-pyridine complex, manganese dioxide, activated manganese dioxide, potassium permanganate, aluminum isopropoxide, aluminum tert-butoxide, lead tetraacetate, ruthenium tetraoxide, N-halocarboxylic acid amide, oxygen, hydrogen peroxide, organic peroxides, halogen, nitric acid, nitrous acid, dimethyl sulfoxide, quinones, silver (I) carbonate, silver (II) carbonate, copper (II) oxide, copper (II) hydroxide, cerium (IV) salts, vanadates, cobalt (II) salts and ozone, at −20° to 180° C., to obtain a cyclopentendione compound of the formula,

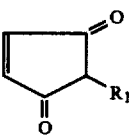

wherein $R_1$ is as defined above; reacting the cyclopentendione compound with a Grignard reagent of the formula,

wherein $R_2$ is as defined above and X is chlorine, bromine or iodine, to obtain an oxocyclopentene compound of the formula,

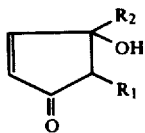

wherein $R_1$ and $R_2$ are as defined above; and reacting the oxocyclopentene compound in the presence of a base selected from the group consisting of hydroxides, carbonates, bicarbonates and acetates of sodium and potassium; basic salts of hydroxides, carbonates, bicarbonates and acetates of calcium and barium; triethylamine or pyridine; and basic ion exchange resins; in an amount of from 0.01 to 10 moles per mole of the oxocyclopentene compound at 0° to 200° C., or in the presence of alumina in an amount of from 0.5 to 30 times the weight of the oxocyclopentene compound at 0° to 150° C.

* * * * *